(12) United States Patent
Worcel

(10) Patent No.: US 8,556,943 B2
(45) Date of Patent: Oct. 15, 2013

(54) LOCK RING FOR OSTEOSYNTHESIS DEVICE AND OSTEOSYNTHESIS DEVICE INCLUDING SUCH RING

(76) Inventor: Alexandre Worcel, Parc de Mongarny (FR)

(*) Notice: Subject to any disclaimer, the term of this patent is extended or adjusted under 35 U.S.C. 154(b) by 538 days.

(21) Appl. No.: 12/815,061

(22) Filed: Jun. 14, 2010

(65) Prior Publication Data

US 2011/0060370 A1  Mar. 10, 2011

Related U.S. Application Data

(63) Continuation-in-part of application No. 12/813,971, filed on Jun. 11, 2010, now abandoned, and a continuation-in-part of application No. PCT/FR2008/001732, filed on Dec. 12, 2008.

(30) Foreign Application Priority Data

Dec. 13, 2007 (FR) ..................................... 07 08686

(51) Int. Cl.
*A61B 17/88* (2006.01)
*A61B 17/80* (2006.01)
(52) U.S. Cl.
USPC .......................................... 606/281; 606/290
(58) Field of Classification Search
USPC .......... 606/280, 281, 286, 289, 290; 411/150, 411/260, 313, 532, 533, 541, 136, 147, 149, 411/371.1, 34, 41, 42, 43, 338, 339
See application file for complete search history.

(56) References Cited

U.S. PATENT DOCUMENTS

| | | | |
|---|---|---|---|
| 5,904,683 A | 5/1999 | Pohndorf et al. | |
| 6,898,918 B2 * | 5/2005 | Eshraghi | 52/787.1 |
| 7,794,482 B2 * | 9/2010 | Mathieu et al. | 606/290 |
| 7,837,717 B2 * | 11/2010 | Deffenbaugh et al. | 606/281 |
| 8,075,602 B2 * | 12/2011 | Lombardo et al. | 606/290 |
| 2007/0010817 A1 | 1/2007 | De Coninck et al. | |
| 2010/0042161 A1 | 2/2010 | Worcel | |
| 2011/0054541 A1 | 3/2011 | Worcel | |
| 2011/0060371 A1 | 3/2011 | Worcel | |

FOREIGN PATENT DOCUMENTS

| | | |
|---|---|---|
| WO | 9801079 A1 | 1/1998 |
| WO | 0112081 A1 | 2/2001 |
| WO | 2004069067 A1 | 8/2004 |
| WO | 2008029032 A2 | 3/2008 |
| WO | 2009/103886 A3 | 8/2009 |
| WO | 2009/112705 A1 | 9/2009 |

OTHER PUBLICATIONS

International Search Report for PCT/FR2008/001732, dated Sep. 21, 2009.

* cited by examiner

*Primary Examiner* — Anu Ramana
(74) *Attorney, Agent, or Firm* — Edgar W. Harlan; Carolyn S. Emore, Esq.; Elmore Patent Law Group, P.C.

(57) ABSTRACT

The invention relates to a locking ring (20) for a threaded holding pin (18) to be screwed into a part of a bone (14), said ring including a first portion (22) having an axial bore (24) for receiving said holding pin, the periphery of said first portion being threaded so as to interact with a holding plate (12), wherein said ring in characterized in that the same further comprises, as an extension to said first portion, a second portion (28), said second portion being deformable and thus capable of blocking said ring on said pin by deformation.

20 Claims, 4 Drawing Sheets

US 8,556,943 B2

LOCK RING FOR OSTEOSYNTHESIS DEVICE AND OSTEOSYNTHESIS DEVICE INCLUDING SUCH RING

RELATED APPLICATIONS

This application is a continuation-in-part of U.S. patent application Ser. No. 12/813,971, filed Jun. 11, 2010, which is a continuation-in-part of International Application No. PCT/FR2008/001732, filed on Dec. 12, 2008, which designated the United States and published in French, which claims priority to French Patent Application No. 0708686, filed on Dec. 13, 2007. The entire teachings of the above applications are incorporated herein by reference.

FIELD OF THE INVENTION

The present invention relates to a lock ring for a fixing pin designed to be screwed into a bone part. It also relates to an assembly comprising not only such a ring but also a collar designed to be inserted into a hole in a fixing plate. Lastly, it relates to an osteosynthesis device.

BACKGROUND OF THE INVENTION

An osteosynthesis device comprises a fixing plate, at least two pins designed to be screwed into two bone parts, and lock rings for anchoring the pins and thus fastening the fixing plate to the two bone parts.

A major problem in this technical field is to devise an osteosynthesis device offering both efficient locking of the pins, to prevent them coming unscrewed when subjected to mechanical stresses or vibrations, and easy unscrewing of the pin when the practitioner wishes to remove the osteosynthesis device.

EP 1 583 478 discloses an osteosynthesis device in which the axis of the pin and that of the lock ring are at an angle relative to each other. In that osteosynthesis device the holes of the fixing plate are threaded and receive an intermediate ring containing a threaded bore to receive a pin and a lock ring.

In order to fit the osteosynthesis device, the practitioner first drills the fixing plate at least two points selected to enable it to be anchored to the bone part, and then drills this bone part with a drill bit guided perpendicular to the fixing plate. Next, he fits the intermediate ring and screws the threaded pin into the bone part to the desired length. He then places the lock ring onto the pin and screws this lock ring into the intermediate ring.

It can be seen that, because of the angular difference between the axis of the pin and that of the lock ring, the lock ring becomes increasingly wedged into the intermediate ring as it is screwed down. This provides an irreversible locking of the pin relative to the fixing plate.

That device is effective but has a number of drawbacks.

In the first place, there is little tolerance in the angular interval between the pin axis and the lock ring axis. Accurate manufacture of the intermediate ring is therefore required, resulting in a high cost of manufacture.

In addition, although this angular interval results in effective locking, it has the disadvantage that this locking action begins as soon as the lock ring begins to be screwed down. The lock ring can therefore sometimes fail to penetrate sufficiently into the fixing plate.

Lastly, in the case of a thin plate (less than 3 mm, for example), the intermediate ring and the lock ring must be inserted partially into the bone part if the device is to be properly anchored. This means that this prior art device cannot be used on the upper bones (arm, forearm, hands, wrist, face), which are too thin.

SUMMARY OF THE INVENTION

It is an object of the invention to overcome the limitations of prior art osteosynthesis devices.

The present invention achieves its object by providing a lock ring for a threaded fixing pin designed to be screwed into a bone piece, said ring comprising a first part having an axial bore to receive said fixing pin, and the periphery of said first part being threaded to engage with a fixing plate; said ring being characterized in that it further comprises, continuing on from said first part, a second part that is thinner than the first part and has a similar axial bore, this second part being deformable and thus able to lock, by deformation, said ring to said pin.

In a preferred embodiment, the bore of the first part of the ring is threaded.

Advantageously, the first part of the ring has a cylindrical or frustoconical external form.

The invention also relates to an assembly comprising a ring according to the invention and a collar, said collar being designed to be inserted into a hole in a fixing plate, the collar having a threaded frustoconical bore corresponding to the thread on the ring.

The collar advantageously comprises a radial slot.

In one particular embodiment, the collar has a convex periphery designed to engage with a concave hole in a fixing plate.

Lastly, the invention relates to an osteosynthesis device comprising a fixing plate having at least two holes, pins designed to be inserted into said holes for screwing into a bone piece, and lock rings or assemblies according to the invention.

Other features and advantages of the invention will become apparent on reading the description given below of one particular embodiment of the invention, given by way of indication, without implying any limitation, with reference to the appended drawings.

DETAILED DESCRIPTION OF THE INVENTION

Figure 1:
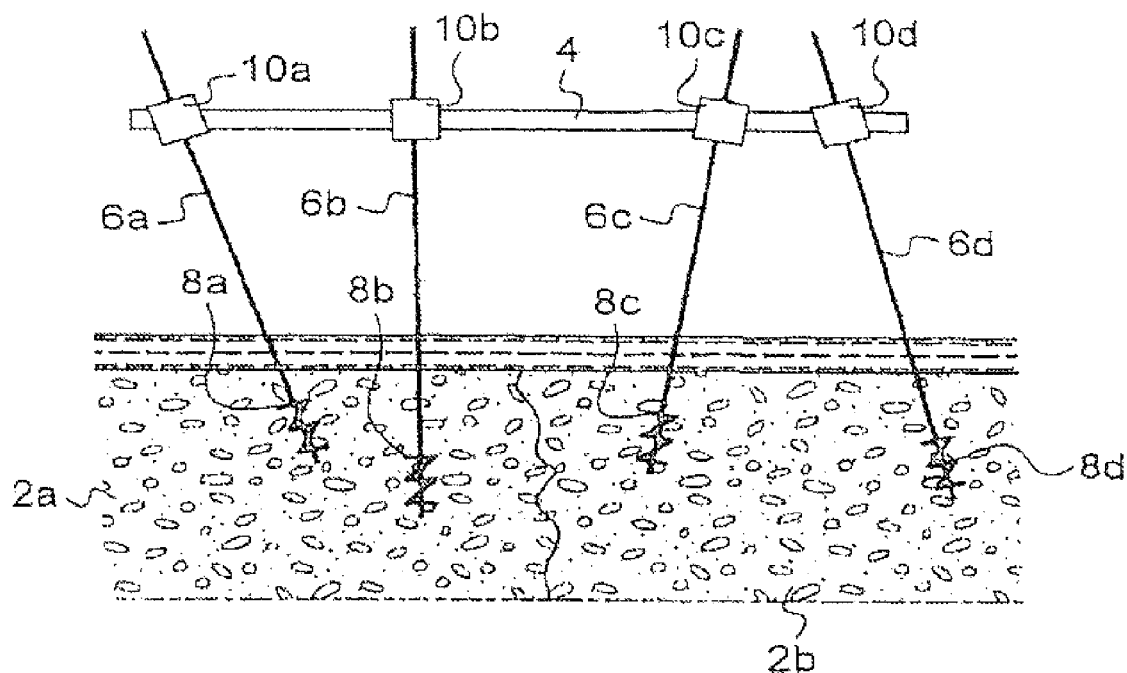
FIG. 1 shows schematically an osteosynthesis device.

FIG. 1 shows schematically an osteosynthesis device for fastening two bone parts 2a, 2b to a fixing plate 4. The fixing plate 4 has holes for pins 6a, 6b, 6c, 6d, to pass through, on at least part of which is a thread 8a, 8b, 8c, 8d for screwing the pin into one of the bone parts. The osteosynthesis device has two pins per bone part but it will be understood that it could have only one pin per bone part in certain cases. It will be noticed that the pins can be screwed in a direction perpendicular to that of the plane of the fixing plate 4. Pin 8b is an example of this. They can also be screwed at an angle to this perpendicular direction. Pins 8a, 8c and 8d are examples of this.

Lock rings 10a, 10b, 10c, 10d are placed in the holes of the fixing plate 4 to fasten the pins to this fixing plate.

Embodiments of a lock ring according to the invention will now be described with reference to FIGS. 2-6.

Figure 2:
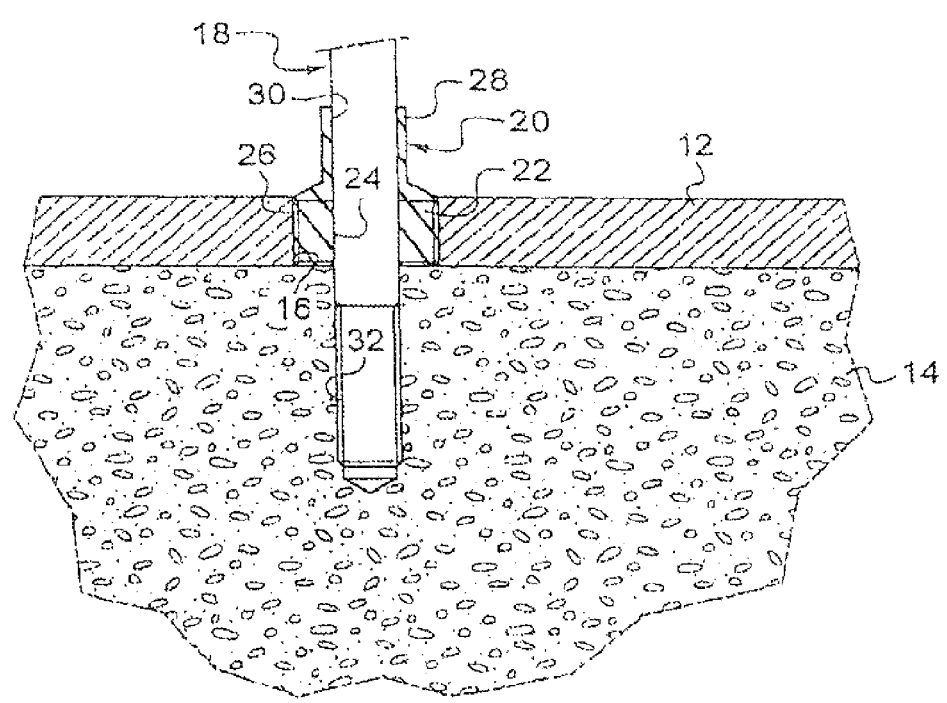
FIG. 2 is a longitudinal section through part of an osteosynthesis device mounted on a bone part comprising a ring in a first embodiment of the invention.

FIG. 2 illustrates part of an osteosynthesis device comprising a ring in a first embodiment of the invention. This figure shows only one pin, but it will be understood that an osteosynthesis device preferably comprises at least two pins in order to unite two bone parts.

In FIG. 2, a fixing plate 12 is placed over a bone part 14. The fixing plate comprises a hole 16 to receive a pin 18 and a lock ring 20.

According to the invention the lock ring 20 comprises a first part 22 which has an axial bore 24 for the passage of the pin 18, which bore may or may not be threaded, the periphery of the first part 22 of the lock ring comprising a thread 26 to enable it to be screwed into the hole in the fixing plate, and a second part 28, continuing on from the first part 22.

In preferred embodiments, the second part is more readily deformed than the first part. In an embodiment, the second part of the lock ring is thinner than the first part. In an embodiment, the second part has a sufficiently thinner wall than the first part that the second part is more easily deformed than the first part. In an embodiment, the first and second parts have substantially similar external diameters, but the wall of the second part is thinner than the wall of the first part. In an embodiment, the second part has an axial bore 30 similar to that of the first part. In an embodiment, the axial bore of the second part has a diameter which is substantially the same as the diameter of the axial bore of the first part.

In an embodiment, the second part is thinner than the first part and has an axial bore similar to that of the first part.

In an embodiment, the end of the first part proximal to the second part (the distal end) is adapted to engage a screwdriver, wrench or other tool suitable for removal of the pin by the practitioner. Preferably, the first part comprises an external driving feature adjacent to the second part. In one embodiment, the external driving feature has an external diameter or dimension which is greater than that of the remainder of the first part. The external driving feature can be a polygonal casing, such as a square or hexagonal casing, for engaging a tool, such as a screwdriver or wrench. The external driving feature can also comprise two or more notches or slots in the periphery of the distal end of first part. In one embodiment, the distal end of the first part comprises three notches separated by 120°. In another embodiment, the external driving feature comprises more than three notches, for example, four, five or six notches. The notches are preferably evenly spaced; that is, for n notches, adjacent notches are preferably separated by 360/n degrees.

The thickness of the second part 28 is selected to suit the material of which the ring 20 is made, so that when the pin and the second part are sheared, the remaining part of the second part deforms and is pushed down against the top of the remaining pin, thus locking the pin relative to the fixing plate. In an embodiment, the second part is made of 316L surgical steel and has a wall thickness of about 0.05 mm to about 1.5 mm, more preferably between about 0.1 mm and about 0.6 mm. In one embodiment, the second part is made of 316L surgical steel and has a wall thickness of about 1 mm.

In an embodiment, the lock ring is made of titanium, titanium alloy, or steel, preferably surgical steel, such as 316L surgical steel. In an embodiment, the lock ring is made of a biodegradable material, such as polylactide (PLA) or another biodegradable polymer.

The osteosynthesis device is installed in the following manner. The practitioner provides or selects a plate comprising at least two holes sufficient for affixing the plate to the bone parts. Alternatively, the practitioner drills holes in the fixing plate at least two points selected to enable it to be fixed to the bone parts. He then drills each bone part, using a drill bit guided perpendicular to the fixing plate. He next pre-positions the lock ring 20 by screwing it part of the way into the hole 16. He can also screw the lock ring 20 all the way into the hole 16, if for example the axial bore of the first part 22 of the lock ring is not threaded. The pin 18, whose bottom part comprises a thread 32, is then screwed into the bone part to the desired length, the lock ring 20, or at any rate its second part, now having a secondary sighting function for guiding the pin as it is screwed in. If the lock ring 20 has merely been pre-positioned, it is now screwed fully into the hole 16.

The practitioner then shears off the pin 18 and the ring 20 approximately at the base of the second part 28—that is, at the junction between the first part 22 and the second part 28. A mark such as a slight groove can be provided at the periphery of the ring in order precisely to define the position of the shearing tool.

The remaining part 34 of the second part 28 of the lock ring 22 is deformed toward the pin 18 by the shearing action. The pin 18 is thus locked relative to the lock ring 22, and hence relative to the fixing plate 12, by a crimping action. Consequently, when the practitioner shears the pin 18 and the ring 20 at the junction between the first part 22 and second part 28, using suitable pliers, the jaws of the pliers initially tend to squeeze the lock ring 20. As the jaws come together, they deform it and finally cut off both the lock ring 20 and the pin 18. A sheared free edge of the second part is thus formed, making a remaining part 34 attached to the first part. Two diametrically opposite portions of this free edge are now pushed toward each other by the shearing action and roughly cover the sheared free end of the pin 18. Thus deformed tightly around the pin 18, the remaining part 34 of the second part 28 of the lock ring 22 locks the pin 18 relative to the lock ring 22 by a crimping action.

Figure 3:
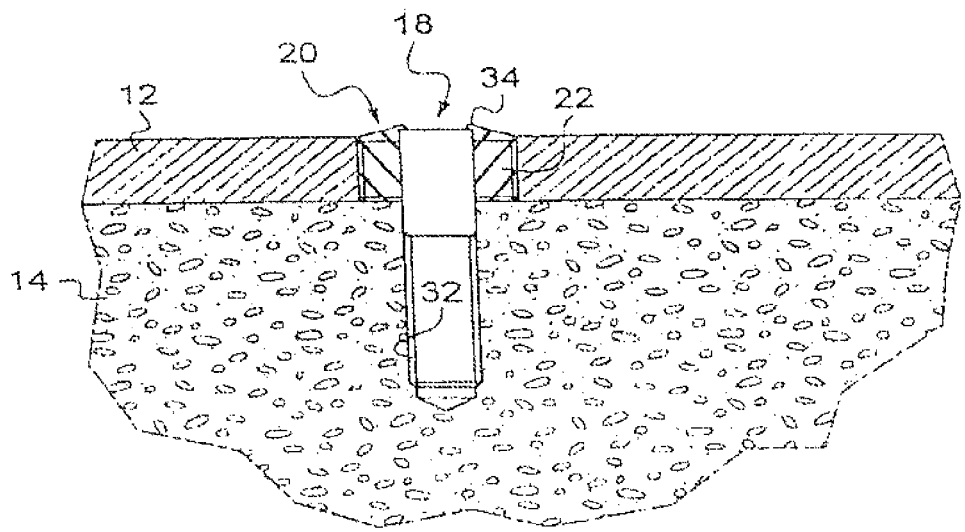
FIG. 3 shows the same device as in FIG. 1 following shearing of the lock ring and pin.

The situation now is that shown in FIG. 3, where elements identical to those in FIG. 2 are given the same references.

The lock ring according to the invention is particularly advantageous in that it offers excellent locking efficiency for small-diameter pins, with diameters of for example from 0.8 to 1.8 mm, which corresponds to the type of pin used on bone parts in the wrist, hand and face.

Thus, experiments have demonstrated a resistance to tension of more than 200 kg on a testing machine able to measure no more than 200 kg with a 4 mm diameter pin and a ring made of 316L surgical steel in which the second part has a thickness of 1 mm. In this test, the ring had no internal thread. It will be appreciated that the resistance to tension would be greatly increased with an internally threaded ring. This would provide in particular excellent resistance to tension, even with small-diameter pins.

Clearly, the lock ring according to the invention is also usable and effective with larger-diameter pins.

Figure 4:
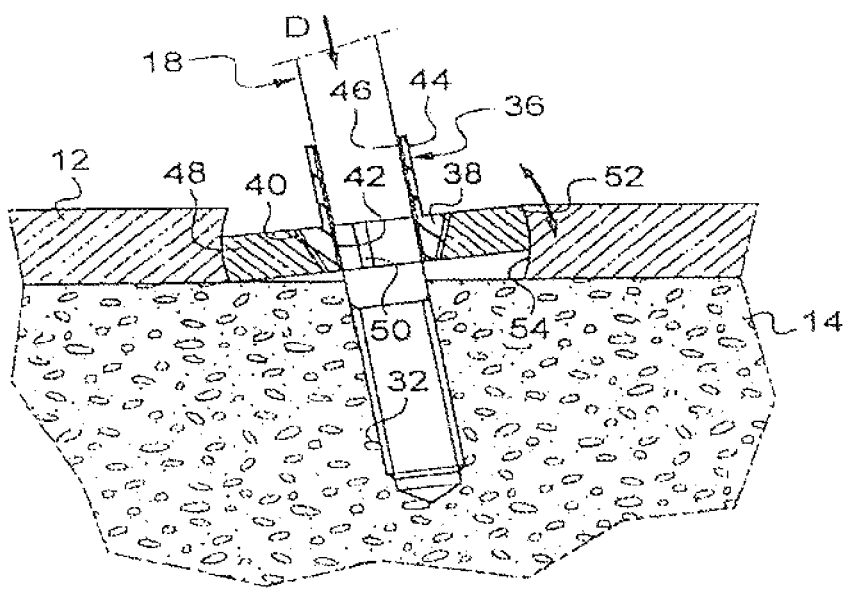
FIG. 4 is a longitudinal section through part of an osteosynthesis device mounted on a bone part comprising a ring in a second embodiment of the invention.
Figure 5:
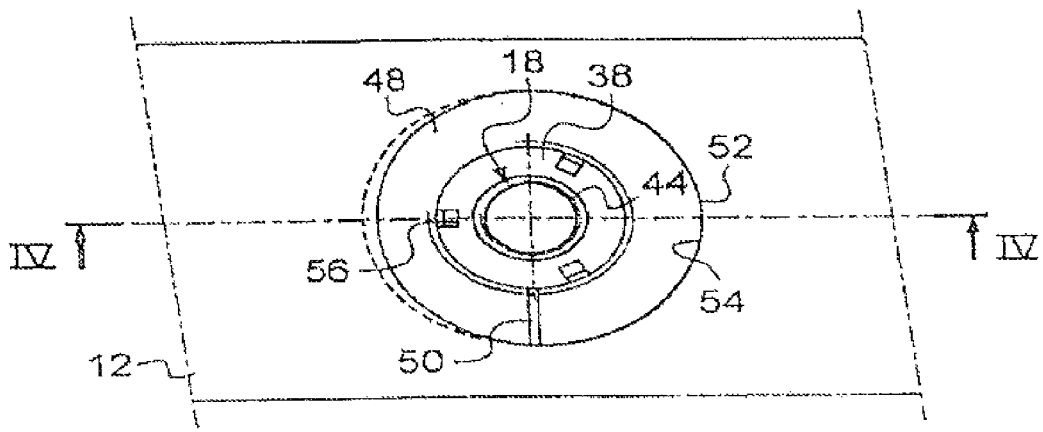
FIG. 5 is a view along D of the device shown in FIG. 4.

FIG. 4 shows a cross section through part of an osteosynthesis device that has a lock ring in accordance with a second embodiment of the invention, and FIG. 5 is a top view along a direction D parallel to the direction of the pin axis.

The lock ring 36 comprises a threaded (thread 40) frusto-conical first part 38 provided with an axial bore 42 and a second part 44, continuing on from the first part, comprising an axial bore 46 similar to that of the first part 38. According to the invention the thickness of the second part is chosen to suit the material used so that this second part is deformable and thus locks the pin, by deformation, when sheared off.

The second embodiment of the invention differs from the first embodiment essentially in that the lock ring is mounted on a collar 48 whose orientation in the orifice 50 of the fixing plate can be adjusted. For this purpose the collar has a convex edge 52 and the hole in the fixing plate 12 has a corresponding concave edge 54. Preferably, the collar has a radial slot 50.

The pin is installed in the same way as in the device described with reference to FIGS. 2 and 3. In one embodiment, the practitioner first selects a plate with at least two holes positioned to be attached to the two bone parts. Preferably the holes have concave edges. In another embodiment, the practitioner introduces the holes into the plate by drilling the plate at least two points. He next forms the concave edge of the hole to permit the subsequent insertion of the collar. He then drills the bone part at the chosen angle using a drill bit. The collar 48 is next placed in the hole in the fixing plate, its insertion being facilitated by the radial slot 50 in the collar 48. The lock ring 36 is screwed at least part of the way onto the collar 48 to immobilize its orientation and thus guide the pin 18. When the pin has been screwed in to the desired length, and the lock ring has been screwed fully down onto the collar 48, the practitioner shears off the lock ring 36 and the pin 18 at the lower part of the second part 44 of the lock ring 36, thus deforming the residual part of this second part and thereby locking the pin 18.

The pin (18) is preferably provided as a headless pin. As can be seen in FIG. 5, shearing of the pin and the second part forms a screw head comprising the remaining end of the pin, the remaining part of the second part and the external driving feature, shown in the figure as three notches (56). The practitioner thus cuts the pin to the required length upon installation of the device. Thus, the invention eliminates the need for a stock of pins of varied lengths.

Figure 6A:
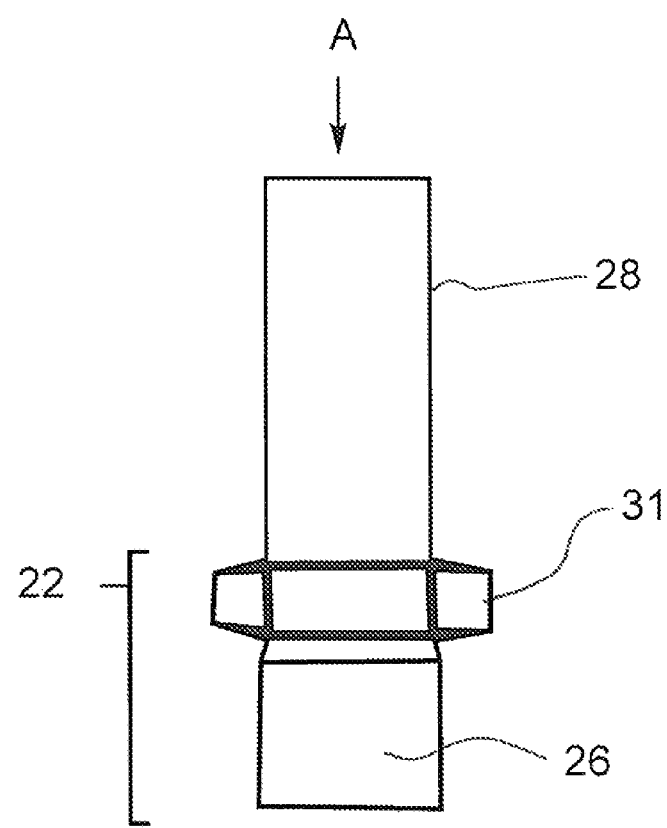
FIG. 6A is an external view of an embodiment of the lock ring of the invention.
Figure 6B:
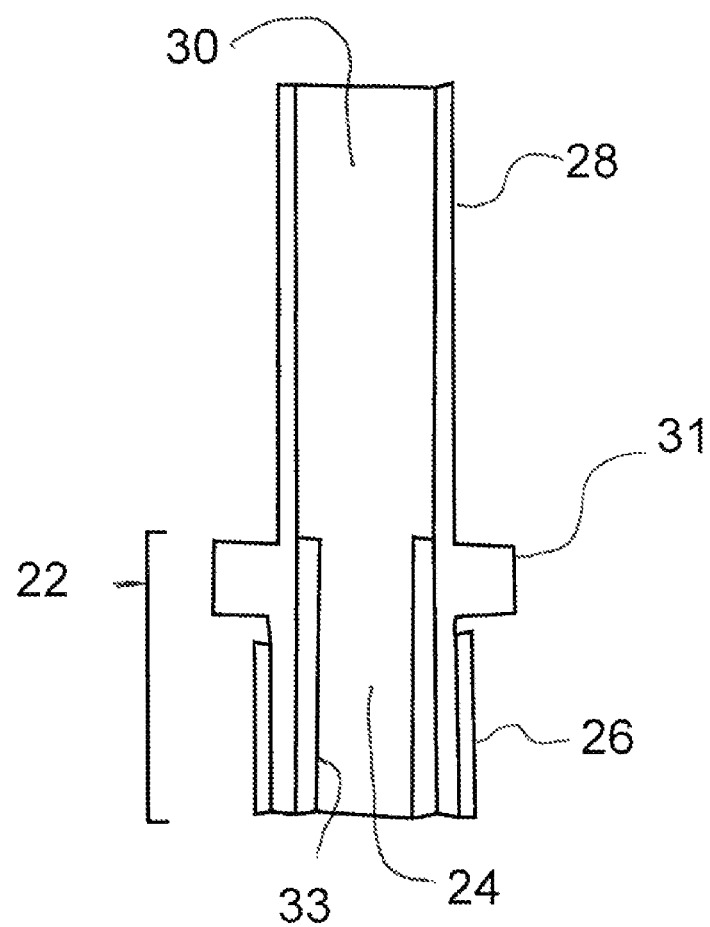
FIG. 6B is a longitudinal section through the lock ring depicted in FIG. 6A.
Figure 6C:
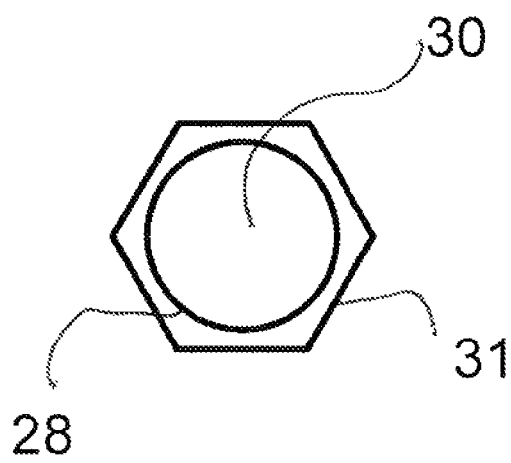
FIG. 6C is a view along axis A of the device shown in FIG. 6A.

Another embodiment of the lock ring of the invention is illustrated in FIGS. 6A-C. FIG. 6A presents an external view of the lock ring, which comprises first part 22 and second part 28. First part 22 comprises external driving feature 31, represented in the figure by an hexagonal casing of which three faces are visible in the figure. First part 22 further comprises external threading 26, which is intended to engage with the threading of a hole in a fixing plate. FIG. 6B is a longitudinal cross-section of the lock ring of FIG. 6A. The lock ring comprises inner bore 30 of second part 28 and inner bore 24 of first part 22. Inner bore 30 and inner bore 24 are cylindrical. First part 22 comprises internal threading 33. It is to be understood that in FIGS. 6A and 6B, the first part includes external driving feature 31, external threaded region 26 and the region, if any, between external driving feature 31 and external threaded region 2. Second part 28 is cylindrical. The portions of first part 22 other than external driving feature 31 are cylindrical. FIG. 6C is a view along axis A as shown in FIG. 6A and shows cylindrical second part 28, inner bore 30 and the hexagonal external driving feature 31.

The plates, lock rings and pins used in the devices of the invention can be provided in a range of sizes. For example, the plates can have a range of thicknesses such as is typical for osteosynthesis plates. For example, in certain embodiments the plates are from about 1 mm to about 2 mm thick. Moreover, the plates can have a range of lengths. In certain embodiments, the plates range from about 5 cm to about 15 cm in length and from about 2.5 cm to about 8 cm in width. In certain embodiments, the width of the plate varies along its length, in certain embodiments having a width from about 2.5 cm to about 3.5 cm near a hole and from about 5 cm to about 7 cm between two holes. The pins can have diameters which are typical for pins used in osteosynthesis devices. In certain embodiments, the pin has a diameter from about 1 mm to about 3 mm, preferably a diameter of from about 2 mm to about 2.5 mm. In certain embodiments, the lock ring has a diameter ranging from about 2 cm to about 5 cm. In certain embodiments, the lock ring has a diameter of about 3 cm. Those of skill in the art can readily select the appropriate plate, lock ring and pin size for the bone parts to be joined.

The osteosynthesis device of the invention preferably comprises a plate with at least two holes configured to join two bone parts, two lock rings as described herein and two pins. However, in certain embodiments, the osteosynthesis device comprises a plate comprising a first means of attachment to a bone part comprising at least one hole, at least one lock ring as described herein and at least one pin. In this embodiment, the device further comprises a second means of attachment to a bone part which is different from the first means. In one embodiment, the second means does not include the lock ring of the invention. The second means can be any means known in the art for attaching a fixing plate to a bone part, for example, a prior art lock ring and pin, a staple, or a pin which is directly screwed into the bone through the plate.

In an embodiment, the invention provides a method of attaching a fixing plate (12) to a bone part (14) in a subject in need of osteosynthesis. The method comprises the steps of:
(a) providing:
  (i) a fixing plate (12) comprising a hole (16);
  (ii) a threaded fixing pin (18) designed to be screwed into the bone part; and
  (iii) a lock ring (20, 36) comprising a first part (22, 38) having an axial bore (24, 42) to receive the fixing pin (18), and the periphery of said first part being threaded to engage with a hole of the fixing plate; said ring being characterized in that it further comprises, continuing on from said first part, a deformable second part (28, 44);
(b) positioning the fixing plate (12) over the bone part (14) such that the at least one hole (16) of the plate (12) overlays the bone part (14);
(c) drilling a hole in the bone part (14), wherein the hole in the bone part (14) is aligned with the hole in the fixing plate (12) of step (c);
(d) partially or completely screwing the lock ring (20, 36) into the hole of the fixing plate (12);
(e) inserting the fixing pin (18) through the axial bore (24, 42) of the lock ring (20, 36) and screwing the fixing pin (18) into the hole in the bone part (14) to a depth sufficient to secure the pin in the bone part;
(f) if the lock ring (20) was only partially screwed into the fixing plate (12) in step (e), screwing the lock ring (20) completely into the hole of the fixing plate (12); and
(g) shearing the fixing pin (18) and the second part (28, 44) of the lock ring (20, 36), thereby deforming a remaining part (34) of the second part (28, 44) toward the fixing pin (18) and locking the fixing pin (18) relative to the fixing plate (12);

thereby affixing the fixing plate (12) to the bone part (14).

Preferably, in step (g), the pin (18) and the second part of the lock ring (28, 44) are sheared simultaneously.

In an embodiment, the process comprises the steps of identifying first and second bone parts in the subject in need of osteosynthesis. In this embodiment, the fixing plate comprises at least two holes, each hole being configured for attachment to one of the bone parts. In this embodiment, steps (a)-(g) are conducted for attachment of the plate to each of the bone parts, thereby fixing and joining the ends of the bone parts. The plate can be affixed to the two bone parts serially or in parallel. In certain embodiments, the plate comprises more than two holes, and the plate is attached to at least one of the bone parts by installation of two or more lock rings and pins according to steps (a)-(g).

In one embodiment, the hole in the fixing plate has a concave edge and is modified prior to step (d) by insertion of a collar as described above, where the collar is oriented within the hole at the desired angle.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A lock ring for a threaded fixing pin designed to be screwed into a bone piece, said ring comprising a first part having an axial bore to receive said fixing pin, and the periphery of said first part being threaded to engage with a fixing plate; and a deformable second part adjacent to the first part, wherein shearing the pin and the ring at the junction between the first part and the second part deforms the remaining part of the second part of the lock ring toward the pin in such a way as to lock the pin with respect to the lock ring by a crimping action.

2. The ring as claimed in claim 1, characterized in that the first part of the ring is internally threaded.

3. The ring as claimed in claim 1, characterized in that the first part has a cylindrical external form.

4. The ring as claimed in claim 1, characterized in that the first part has a frustoconical external form.

5. An assembly comprising a ring as claimed in claim 4 and a collar, said collar being designed to be inserted into a hole in a fixing plate, the collar having a threaded frustoconical bore corresponding to the thread on the ring, and a radial slot.

6. The assembly as claimed in claim 5, characterized in that the collar has a convex periphery designed to engage with a concave hole in a fixing plate.

7. An osteosynthesis device comprising a fixing plate having at least two holes, at least two pins designed to be inserted into said holes for screwing into a bone piece and assemblies as claimed in claim 5.

8. The ring of claim 1, wherein the wall of the second part (28, 44) is thinner than the wall of the first part.

9. The ring of claim 1, wherein the axial bore of the second part is substantially the same diameter as the axial bore of the first part.

10. The ring of claim 1, wherein the first part comprises an external driving feature.

11. An osteosynthesis device comprising a fixing plate having at least two holes, pins designed to be inserted into said holes for screwing into a bone piece, and lock rings as claimed in claim 1.

12. The osteosynthesis device of claim 11, wherein the pins are headless.

13. A method of attaching a fixing plate to a bone part in a subject in need of osteosynthesis of first and second bone parts, the method comprising the steps of:
（a) providing:
    (i) a fixing plate with at least two holes, wherein the holes are positioned for attachment of the plate to the two bone parts,
    (ii) a threaded fixing pin designed to be screwed into the first bone part, (iii) the lock ring of claim 1;
(b) positioning the fixing plate over the first bone part such that at least one hole of the plate overlays the first bone part;
(c) drilling at least one hole in the first bone part, wherein the hole in the first bone part is aligned with the hole in the fixing plate of step (c);
(d) partially or completely screwing the lock ring into the hole of the fixing plate which is aligned with the hole in the first bone part;
(e) inserting the fixing pin through the axial bore of the lock ring and screwing the fixing pin into the hole in the first bone part to a depth sufficient to secure the pin in the bone part;
(f) if the lock ring was only partially screwed into the fixing plate in step (e), screwing the lock ring completely into the hole of the fixing plate; and
(g) shearing the fixing pin and the second part of the lock ring, thereby deforming a remaining part of the second part toward the fixing pin and locking the fixing pin relative to the fixing plate;
thereby affixing the fixing plate to the first bone part.

14. The method of claim 13, wherein steps (a)-(g) are repeated for the second bone part.

15. The method of claim 13, wherein the hole of the fixing plate has a concave edge and a collar having a threaded frustoconical bore corresponding to the thread on the lock ring, and a radial slot is inserted into the hole prior to step (d).

16. The method of claim 15, wherein the collar has a convex periphery designed to engage with the concave edge of the hole in the fixing plate.

17. The method of claim 15, wherein the first part of the lock ring has a frustoconical external form.

18. The method of claim 13, wherein the first part of the lock ring is internally threaded.

19. The method of claim 13, wherein the first part of the lock ring has a cylindrical external form.

20. The method of claim 13, wherein the pin is headless.

* * * * *